(12) United States Patent
DuPuis

(10) Patent No.: US 7,029,661 B1
(45) Date of Patent: Apr. 18, 2006

(54) COSMETIC COMPOSITION WITH A FIXING AND/OR CONDITIONING POLYMER CONTAINING A SPECIFIC ACRYLIC COPOLYMER

(75) Inventor: Christine DuPuis, Paris (FR)

(73) Assignee: L'Oreal, (FR)

( * ) Notice: Subject to any disclaimer, the term of this patent is extended or adjusted under 35 U.S.C. 154(b) by 0 days.

(21) Appl. No.: 09/172,853

(22) Filed: Oct. 15, 1998

Related U.S. Application Data

(63) Continuation of application No. 08/694,591, filed on Aug. 9, 1996.

(30) Foreign Application Priority Data

Aug. 11, 1995 (FR) .................................. 95 09774

(51) Int. Cl.
*A61K 7/11* (2006.01)
*A61K 47/32* (2006.01)

(52) U.S. Cl. .............................. 424/70.16; 424/DIG. 1; 424/DIG. 2

(58) Field of Classification Search ................ 424/401, 424/70.16, 47, DIG. 1, DIG. 2, 78.31
See application file for complete search history.

(56) References Cited

U.S. PATENT DOCUMENTS

| 4,085,264 A | 4/1978 | Seib et al. |
| 4,789,713 A | 12/1988 | Sanner et al. |
| 4,874,604 A | 10/1989 | Sramek |
| 5,160,730 A | 11/1992 | Dubief et al. |
| 5,306,484 A | 4/1994 | Potthoff-Karl et al. |
| 5,413,775 A | 5/1995 | Hatfield et al. |

FOREIGN PATENT DOCUMENTS

| DE | 4314305 | 11/1994 |
| EP | 0288012 | 10/1988 |
| EP | 0320218 | 6/1989 |
| EP | 0323715 | 7/1989 |
| EP | 0379082 | 7/1990 |
| EP | 0424260 | 4/1991 |
| EP | 0590604 | 4/1994 |
| FR | 2351135 | 12/1977 |
| FR | 2697160 | 4/1994 |
| JP | SHO 53-12429 | 2/1978 |
| JP | 6-207073 | 7/1994 |
| JP | HEI 9-110630 | 4/1997 |
| WO | WO 9221316 | 12/1992 |
| WO | WO 9528909 | 11/1995 |

OTHER PUBLICATIONS

English lanuage Derwent Abstract of FR 2697160.
English language Derwent Abstract of DE 4314305.
Chemical Abstracts, vol. 89, No. 14, p. 517, Abstract No. 117546m, Oct. 2, 19978, "Hair-Setting Preparation."
Joseph P. Pavlichki, "Novel New Hair Spray Resin Utilizing Aqueous Dispersion Technology for 0-80% VOC Systems", Amerchol Corporation, Edison, New Jersey.
Amerhold™ DR-25: The water-based hair spray technology that performs beautifully.
Advertisement in *Spray Technology and Marketing*—"Amerchol Mixes Resins to Improve 55% VOC Hair Sprays", Sep., 1998, vol. 8, No. 9.
Product label—"Avon Techniques Hair Spray For Extra Hold and All-Over Control," 1997 (based on information and belief).
Product label—"Avon Techniques Finishing Hair Spray for Natural Hold and Control," launch date Jul. 1997 (based on information and belief).
Spray Technology and Marketing for Nov. 1997, "Avon's Techniques Hair Care Products Feature Performance Boosters", p. 16.
Cosmetic Research USA News, Sep. 1997.
"Aqueous Dispersion Hair-Spray Resin", Cosmetics and Toiletries Magazine, vol. 110, Jun. 1995, Joseph P. Pavlichko.
"Acudyne™ 255 hair fixative polymer for low VOC Hair Sprays," Rohm and Haas Company, pp. 1-11, Sep. 1994.

*Primary Examiner*—Edward J. Webman
(74) *Attorney, Agent, or Firm*—Finnegan, Henderson, Farabow, Garrett & Dunner L.L.P.

(57) ABSTRACT

The invention relates to a sprayable or vaporizable cosmetic composition, in particular in the form of an aerosol, comprising, in a cosmetically acceptable aqueous or aqueous/alcoholic medium, at least one fixing and/or conditioning polymer and at least one alkyl acrylate/alkyl methacrylate/acrylic acid copolymer.

24 Claims, No Drawings

COSMETIC COMPOSITION WITH A FIXING AND/OR CONDITIONING POLYMER CONTAINING A SPECIFIC ACRYLIC COPOLYMER

This is a continuation of application Ser. No. 08/694,591, filed Aug. 9, 1996, which is incorporated herein by reference.

The invention relates to a readily sprayable and/or vaporizable cosmetic composition comprising, in a cosmetically acceptable aqueous or aqueous/alcoholic medium at least one polymer selected from a fixing polymer and a conditioning polymer and at least one specific acrylic copolymer and to the use of this specific copolymer for improving the vaporization or the spraying of the composition comprising at least one fixing and/or conditioning polymer.

Hair compositions to be sprayed onto the hair are essentially composed of a solution, in most cases aqueous/alcoholic, and of a polymer, optionally as a mixture with various cosmetic adjuvants. This solution is packaged either in a pump-action spray or in an appropriate aerosol container which is pressurized using a propellant gas.

For essentially ecological reasons, a search is underway to reduce the compounds which are volatile at atmospheric pressure, known as VOCs (Volatile Organic Compounds), present in the compositions. The VOCs are mainly the propellants and certain solvents, such as ethanol.

Thus, legislation in certain countries has laid down a minimum VOC content in aerosol cosmetic compositions. In order to decrease the amount of VOC, attempts have been made to replace solvents, such as ethanol, by water. These modifications can result in problems, in particular with respect to the quality of the spraying of the spray. The sprayed liquid particles are not fine, the spray is often narrow, i.e., non-diffuse, and the formation of a slight foam and/or bubbles can take place.

As the spraying is an essential component in the final quality of a composition to be sprayed onto hair, it is essential to overcome these disadvantages in order to obtain good distribution over the whole of the hair and correct fixing and/or conditioning of the hair.

European Application EP-A-590,604 describes an aqueous composition based on an anionic acrylic copolymer and hair spray compositions comprising this aqueous composition based on an anionic acrylic copolymer. This polymer-based composition is compatible with many solvents. It exhibits good cosmetic properties. However, the appearance of the sprays obtained is still unsatisfactory.

The present inventors have discovered, unexpectedly and surprisingly, that, by combining the polymers commonly used in compositions for form retention and/or for conditioning of the hairstyle with the specific anionic copolymer described above in EP-A-590,604, it is possible to obtain aqueous or aqueous/alcoholic compositions which are readily sprayable and/or vaporizable.

The subject of the present invention is therefore a cosmetic composition comprising, in a cosmetically acceptable aqueous or aqueous/alcoholic medium, at least one polymer selected from a fixing polymer and a conditioning polymer and at least one acrylic copolymer formed from (a) approximately 35 to 75% by weight of an alkyl acrylate, (b) approximately 25 to 65% by weight of alkyl methacrylate and (c) approximately 1 to 15% by weight of at least one ethylenic carboxylic acid having from 3 to 5 carbon atoms, the alkyl radicals having from 1 to 5 carbon atoms and these percentages being expressed by weight with respect to the total weight of copolymer.

Another subject of the invention is the use of the copolymer described above for improving the quality of the vaporization or of the spraying of cosmetic compositions packaged, for example, in a pump-action spray or in an aerosol and comprising a fixing and/or conditioning polymer.

The sprays obtained with the compositions according to the invention can be more diffuse and the drops can be finer. The compositions can also show no or very little foaming.

In the context of the present application, cosmetic compositions for form retention of the hairstyle is understood to mean any composition having the function of temporarily fixing the shape of the hairstyle, such as, for example, lacquers, hair-setting compositions and styling sprays. Fixing power of the composition denotes the ability of the latter to give the hair a cohesion such that the initial hair shaping of the hairstyle is retained.

Fixing polymer is understood to mean and polymer having the function of temporarily fixing the shape of the hairstyle. In the context of the present application, conditioning polymer is understood to mean any polymer having the function of improving the cosmetic properties of hair, in particular softness, disentangling, feel or static electricity.

According to the invention, the acrylic copolymer described above generally has a glass transition temperature of 10 to 50° C. approximately and preferably 20 to 40° C. and more particularly still 25 to 35° C. This copolymer can exhibit a number-average molecular weight of 10,000 to 50,000 and preferably 20,000 to 40,000.

The alkyl acrylate is preferably chosen from methyl acrylate, ethyl acrylate, propyl acrylate and butyl acrylate. Ethyl acrylate is particularly preferred.

The concentration of alkyl acrylate is preferably 40 to 70% by weight and more particularly 50 to 60% by weight with respect to the total weight of the copolymer.

The alkyl methacrylate is preferably chosen from methyl methacrylate, ethyl methacrylate, propyl methacrylate and butyl methacrylate. Methyl methacrylate is particularly preferred.

The concentration of alkyl methacrylate is preferably from 30 to 50% by weight and more particularly from 30 to 40% by weight with respect to the total weight of the copolymer.

The preferred ethylenic carboxylic acids are acrylic acid, methacrylic acid, crotonic acid, itaconic acid or their mixtures. Acrylic acid and methacrylic acid are particularly preferred. According to the invention, it is possible to use salts of these carboxylic acids.

The concentration of ethylenic carboxylic acids, or of their salts, is preferably from 5 to 15% by weight and more particularly from 8 to 12% by weight with respect to the total weight of the copolymer.

In a particularly preferred embodiment of the invention, acrylic acid is used with methacrylic acid, each in a concentration of from 2 to 10% by weight, the total of these two acids not exceeding 15% by weight of the total weight of the copolymer.

The copolymer can also contain small amounts, i.e., preferably less than 10%, more preferably less than 5% and most preferably less than 2%, of a polymerizable monomer other than those mentioned above.

The copolymer can be used in the form of an aqueous dispersion. Generally, the dispersion then comprises at least 0.05% of surfactant making possible the dispersing and the maintenance in dispersion of the polymer.

According to the invention, it is possible to use any type of surfactant in the said dispersion but preferably a non-ionic surfactant and more particularly polyoxyalkylenated ($C_6$–$C_{12}$)alkyl phenols.

The mean size of the particles of the copolymer in the dispersion is preferably from 0.1 to 1 micron.

According to a particularly preferred embodiment of the invention, use is made of a copolymer comprising 50 to 60% by weight of ethyl acrylate, 30 to 40% by weight of methyl methacrylate, from 2 to 10% by weight of acrylic acid and from 2 to 10% by weight of methacrylic acid, the total concentration of acrylic and methacrylic acid not exceeding 15% by weight with respect to the total weight of the acrylic copolymer.

Such a copolymer is, for example, described in European Patent Application EP-A-590,604, the disclosure of which is hereby incorporated by reference.

An aqueous dispersion of the acrylic copolymer described above comprising 25% by weight of ethyl acrylate/methyl methacrylate/methacrylic acid/acrylic acid copolymer having a glass transition temperature of approximately 30° C. is in particular sold under the name Amerhold DR-25 by the company Amerchol.

According to the invention, the carboxylic acid functional groups of the acrylic copolymer can be partially or completely neutralized.

According to the invention, it is possible to use any fixing and/or conditioning polymer known per se. In particular, it is possible to use a fixing and/or conditioning polymer chosen from anionic, cationic, amphoteric and non-polymers and their mixtures.

The conditioning polymers are, preferably chosen from cationic and amphoteric polymers and their mixtures. The fixing and/or conditioning polymers can be used in the dissolved form or in the latex form (aqueous dispersion of solid polymer particles).

Thus, the anionic polymers generally used are polymers containing groups derived from carboxylic, sulphonic or phosphoric acid and have a number-average molecular weight of from approximately 500 to 5,000,000.

1) The carboxyl groups are introduced by unsaturated mono-or dicarboxylic acid monomers such as those corresponding to the formula (I):

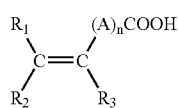

(I)

in which n is an integer from 0 to 10, A denotes a methylene group, optionally connected to the carbon atom of the unsaturated group or to the neighbouring methylene group, when n is greater than 1, via a heteroatom, such as oxygen or sulphur, $R_1$ denotes a hydrogen atom or a phenyl or benzyl group, $R_2$ denotes a hydrogen atom or a lower alkyl or carboxyl group and $R_3$ denotes a hydrogen atom, a lower alkyl group or a —$CH_2$—COOH, phenyl or benzyl group. In the above-mentioned formula, a lower alkyl radical preferably denotes a group having 1 to 4 carbon atoms and in particular methyl and ethyl.

The preferred anionic polymers containing carboxyl groups according to the invention are:

A) Homo- or copolymers of acrylic or methacrylic acid or their salts and in particular the products sold under the names Versicol E or K by the company Allied Colloid or Ultrahold by the company BASF, copolymers of acrylic acid and of acrylamide sold in the form of their sodium salt under the names Reten 421, 423 or 425 by the Company Hercules or the sodium salts of polyhydroxycarboxylic acids.

B) Copolymers of acrylic or methacrylic acid with a monoethylenic monomer, such as ethylene, styrene, vinyl esters or esters of acrylic or methacrylic acid, optionally grafted onto a polyalkylene glycol, such as polyethylene glycol, and optionally crosslinked. Such polymers are described in particular in French Patent FR 1,222,944 and German Application DE 2,330,956 the disclosures of which are hereby incorporated by reference, the copolymers of this type containing, in their chain, an optionally N-alkylated and/or -hydroxyalkylated acrylamide unit, such as described in particular in Luxembourgian Patent Applications 75370 and 75371, the disclosures of which are hereby incorporated by reference, or sold under the name Quadramer by the Company American Cyanamid. Mention may also be made of copolymers of acrylic acid and of $C_1$–$C_4$ alkyl methacrylate and terpolymers of vinylpyrrolidone, of acrylic acid and of $C_1$–$C_{20}$ alkyl methacrylate, for example lauryl methacrylate, such as that sold by the company ISP under the name Acrylidone LM, and methacrylic acid/ethyl acrylate/tert-butyl acrylate terpolymers, such as the product sold under the name Luvimer 100 P by the company BASF.

C) Copolymers derived from crotonic acid, such as those containing, in their chain, vinyl acetate or propionate units and optionally other monomers, such as allyl or methylal esters, vinyl ether or vinyl ester of a linear or branched saturated carboxylic acid containing a long hydrocarbon chain, such as those containing at least 5 carbon atoms, it being possible for these polymers optionally to be grafted and crosslinked, or alternatively a vinyl, allyl or methallyl ester of an α- or β-cyclic carboxylic acid. Such polymers are described, inter alia, in French Patents 1,222,944, 1,580,545, 2,265,782, 2,265,781, 1,564,110 and 2,439,798, the disclosures of which are hereby incorporated by reference. Commercial products coming within this class are the resins 28-29-30, 26-13-14 and 28-13-10 sold by the company National Starch.

D) Polymers derived from maleic, fumaric or itaconic acids or anhydrides with vinyl esters, vinyl ethers, vinyl halides, phenylvinyl derivatives or acrylic acid and its esters; these polymers can be esterified. Such polymers are described in particular in U.S. Patent Nos. U.S. Pat. Nos. 2,047,398, 2,723,248 and 2,102,113 and British Patent GB 839,805, the disclosures of which are hereby incorporated by reference, and in particular those sold under the names Gantrez AN or ES by the company ISP.

Polymers also coming within this class are copolymers of maleic, citraconic or itaconic anhydrides and of an allyl or methallyl ester, optionally containing an acrylamide or methacrylamide group, an α-olefin, acrylic or methacrylic esters, acrylic or methacrylic acids or vinylpyrrolidone in their chain; the anhydride functional groups are monoesterified or monoamidified. These polymers are, for example, described in French Patents 2,350,384 and 2,357,241 assigned to the present assignee, the disclosures of which are hereby incorporated by reference.

E) Polyacrylamides containing carboxylate groups.

2) The polymers comprising sulpho groups are polymers containing vinylsulpho, styrenesulpho, naphthalenesulpho or acrylamidoalkylsulpho units.

These polymers can in particular be selected from:

salts of polyvinylsulphonic acid having a number-average molecular weight of from approximately 1000 to 100,000, as well as copolymers with an unsaturated comonomer, such as acrylic or methacrylic acids and their esters, as well as acrylamide or its derivatives, vinyl ethers and vinylpyrrolidone.

Salts of polystyrenesulphonic acid, the sodium salts having a number-average molecular weight of approximately 500,000 and of approximately 100,000 sold respectively under the names Flexan 500 and Flexan 130 by National Starch. These compounds are described in French Patent FR 2,198,719, the disclosure of which is hereby incorporated by reference.

Salts of polyacrylamidesulphonic acids, those mentioned in U.S. Pat. No. 4,128,631, the disclosure of which is hereby incorporated by reference, and more particularly salts of polyacrylamidoethylpropanesulphonic acid.

According to the invention, the anionic polymers are preferably chosen from copolymers of acrylic acid, such as the acrylic acid/ethyl acrylate/N-tert-butylacrylamide terpolymer sold under the name Ultrahold Strong by the company BASF, copolymers derived from crotonic acid, such as the vinyl acetate/vinyl tert-butylbenzoate/crotonic acid terpolymers and the crotonic acid/vinyl acetate/vinyl neododecanoate terpolymers sold under the name Resin 28-29-30 by the company National Starch, polymers derived from maleic, fumaric or itaconic acids or anhydrides with vinyl esters, vinyl ethers, vinyl halides, phenylvinyl derivatives or acrylic acid and its esters, such as the monoesterified maleic anhydride/methyl vinyl ether copolymer sold under the name Gantrez ES 425 by the company ISP, copolymers of methacrylic acid and of methyl methacrylate sold under the name Eudragit L by the company Rohm Pharma, the copolymer of methacrylic acid and of ethyl acrylate sold under the name Luvimer Maex by the company BASF, the vinylpyrrolidone/acrylic acid/lauryl methacrylate terpolymer sold under the name Acrylidone LM by the company ISP or the methacrylic acid/ethyl acrylate/tert-butyl acrylate terpolymer sold under the name Luvimer 100 P by the company BASF.

The cationic poly which can be used according to the present invention are preferably chosen from polymers containing primary, secondary, tertiary and/or quaternary amine groups forming part of the polymer chain or directly connected to the latter and having a number-average molecular weight of from 500 to approximately 5,000,000 and preferably from 1000 to 3,000,000.

In the context of fixing cationic polymers, preference is given to cationic polymers with a conductivity of less than or equal to 1 mohm$^{-1}$ cm$^{-1}$ and which have a viscosity, at 1% in water, of less than 20 cps (20 mPa·s). The viscosity is measured using a Rheomat RM 180 (Contraves TV, rotor 1) from Mettler.

Mention may more particularly be made, among these polymers, of the following cationic polymers:

(1) Homopolymers or copolymers derived from acrylic or methacrylic esters or amides and containing at least one of the units of following formulae:

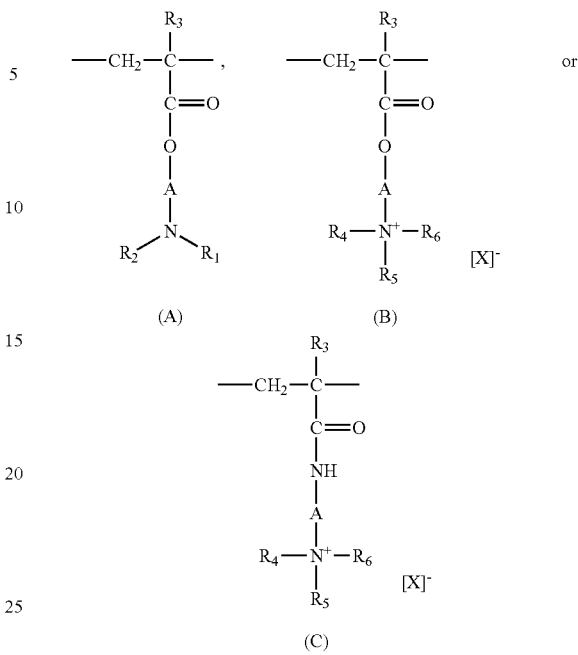

in which:

$R_3$ denotes H or $CH_3$;

A is a linear or branched alkyl group containing 1 to 6 carbon atoms or a hydroxyalkyl group containing 1 to 4 carbon atoms;

$R_4$, $R_5$ and $R_6$, which are identical or different, represent an alkyl group having from 1 to 18 carbon atoms or a benzyl radical;

$R_1$ and $R_2$ represent hydrogen or an alkyl group having from 1 to 6 carbon atoms;

X denotes a methyl sulphate anion or a halide, such as chloride or bromide.

The copolymers of the family (1) additionally contain one or a number of units deriving from comonomers which can be chosen from the family of acrylamides, methacrylamides, diacetone acrylamides, acrylamides and methacrylamides substituted on the nitrogen by lower alkyls, acrylic or methacrylic acids or their esters, vinyllactams, such as vinylpyrrolidone or vinylcaprolactam, or vinyl esters.

Thus, mention may be made, among these copolymers of the family (1), of:

the copolymer of acrylamide and of dimethylaminoethyl methacrylate, quaternized with dimethyl sulphate, sold under the name Hercofloc by the company Hercules, copolymers of acrylamide and of methacryloyloxyethyltrimethylammonium chloride described, for example, in European Patent Application EP-A-080,976, the disclosure of which is hereby incorporated by reference, and sold under the name Bina Quat P 100 by the company Ciba-Geigy, the copolymer of acrylamide and of methacryloyloxyethyltrimethylammonium methyl sulphate sold under the name Reten by the company Hercules, optionally quaternized vinylpyrrolidone/dialkylaminoalkyl acrylate or methacrylate copolymers, such as the products sold under the name "Gafquat" by the company ISP, such as, for example, "Gafquat 734" or "Gafquat 755", or alternatively the products named "Copolymer 845, 958 and 937". These polymers are described in detail in French Patents 2,077,143 and 2,393,573, the disclosures of which are hereby incorporated by reference, the dimethylaminoethyl methacrylate/vinylcaprolactam/vinylpyrrolidone terpolymer, such as the product sold under the name Gaffix VC 713 by the company ISP, and the quaternized dimethylaminopropyl-methacrylamide/vinylpyrrolidone copolymer, such as the product sold under the name "Gafquat HS 100" by the company ISP.

(2) Quaternized polysaccharides, described more particularly in U.S. Pat. Nos. 3,589,578 and 4,031,370, the disclosures of which are hereby incorporated by reference, such as the product sold under the name Jaguar C 13 S by the company Meyhall.

(3) Quaternary copolymers of vinylpyrrolidone and of vinylimidazole.

(4) Chitosans or their salts;

the salts which can be used are in particular chitosan acetate, lactate, glutamate, gluconate or pyrrolidonecarboxylate.

Mention may be made, among these compounds, of chitosan having a degree of deacetylation of 90.5% sold under the name Kytan Crude Standard by the company Aber Technologies or chitosan pyrrolidonecarboxylate sold under the name Kytamer PC by the company Amerchol.

The amphoteric polymers which can be used in accordance with the invention can be chosen from polymers containing A and B units distributed statistically in the polymer chain, where A denotes a unit deriving from a monomer containing at least one basic nitrogen atom and B denotes a unit deriving from an acidic monomer containing one or a number of carboxyl or sulpho groups or alternatively A and B can denote groups deriving from zwitterionic carboxybetaine or sulphobetaine monomers.

A and B can also denote a cationic polymer chain containing primary, secondary, tertiary or quaternary amine groups, in which at least one of the amine groups carries a carboxyl or sulpho group connected via a hydrocarbon radical or alternatively A and B form part of a chain of a polymer containing an α, β-dicarboxy ethylene unit in which one of the carboxyl groups has been reacted with a polyamine containing one or a number of primary or secondary amine groups.

The more particularly preferred amphoteric polymers corresponding to the definition given above are chosen from the following polymers:

(1) Polymers resulting from the copolymerization of a monomer derived from a vinyl compound carrying a carboxyl group, such as more particularly acrylic acid, methacrylic acid, maleic acid or α-chloroacrylic acid, and of a basic monomer derived from a substituted vinyl compound containing at least one basic atom, such as more particularly dialkylaminoalkyl methacrylate and acrylate or dialkylaminoalkylmethacrylamide and acrylamide. Such compounds are described in U.S. Pat. No. 3,836,537, the disclosure of which is hereby incorporated by reference.

(2) Polymers derived from diallyldialkylammonium and from at least one anionic monomer, such as polymers containing approximately 60 to approximately 99% by weight of units derived from a quaternary diallyldialkylammonium monomer, in which the alkyl groups are independently chosen from alkyl groups having 1 to 18 carbon atoms and in which the anion is derived from an acid having an ionization constant greater than $10^{-13}$, and 1 to 40%, by weight of this polymer, of an anionic monomer chosen from acrylic or methacrylic acids, the number-average molecular weight of this polymer being from approximately 50,000 to 10,000,000, determined by gel permeation chromatography. Such polymers are described in European Application EP-A269,243, the disclosure of which is hereby incorporated by reference.

The preferred polymers are, inter alia, polymers containing alkyl groups selected from groups having 1 to 4 carbon atoms and more particularly methyl and ethyl groups.

Among these polymers, copolymers of dimethyldiallylammonium or of diethyldiallylammonium chloride and of acrylic acid are particularly preferred. These polymers are, for example, sold under the names "Merquat 280" and "Merquat 295" by the company Merck. It is also possible to use the dimethyldiallylammonium chloride/acrylic acid/acrylamide terpolymers sold under the name "Merquat Plus 3330" by the company Merck.

(3) Polymers containing units deriving:
  a) from at least one monomer selected from acrylamides or methacrylamides substituted on the nitrogen by an alkyl radical,
  b) from at least one acidic comonomer containing one or a number of reactive carboxyl groups, and
  c) from at least one basic comonomer, such as esters containing primary, secondary, tertiary and/or quaternary amine substituents of acrylic and methacrylic acids and the product from the quaternization of dimethylaminoethyl methacrylate with dimethyl or diethyl sulphate.

The more particularly preferred N-substituted acrylamides or methacrylamides according to the invention are the groups in which the alkyl radicals contain from 2 to 12 carbon atoms and more particularly N-ethylacrylamide, N-tert-butylacrylamide, N-tert-octylacrylamide, N-octylacrylamide, N-decylacrylamide or N-dodecylacrylamide, and the corresponding methacrylamides.

The acidic comonomers are more particularly chosen from acrylic, methacrylic, crotonic, itaconic, maleic and fumaric acids and the alkyl monoesters, having 1 to 4 carbon atoms, of maleic or fumaric acids or anhydrides.

The preferred basic comonomers are aminoethyl, butylaminoethyl, N,N'-dimethylaminoethyl and N-tert-butylaminoethyl methacrylates.

Use is particularly made of copolymers whose CTFA name (4th Ed., 1991) is Octylacrylamide/acrylates/butylaminoethyl methacrylate copolymer, such as the products sold under the name Amphomer or Lovocryl 47 by the company National Starch.

(4) Partially or totally alkylated and crosslinked polyaminoamides deriving from polyaminoamides of general formula (II):

$$—[—CO—R_{10}—CO—Z—]—\quad\quad(II)$$

in which $R_{10}$ represents a divalent radical derived from a saturated dicarboxylic acid, from an aliphatic mono- or dicarboxylic acid containing an ethylenic double bond, from an ester of a lower alkanol having 1 to 6 carbon atoms of these acids or from a radical deriving from the reaction of any one of the said acids with a bisprimary or bissecondary amine and Z denotes a radical from a bisprimary or mono- or bissecondary polyalkylenepolyamine and preferably represents:

a) in the proportions of 60 to 100 mol %, the radical (III)

$$—NH—[—(CH_2)_x—NH—]_n—\quad\quad(III)$$

where x=2 and n=2 or 3 or alternatively x=3 and n=2, this radical deriving from diethylenetriamine, triethylenetetraamine or dipropylenetriamine;

b) in the proportions of 0 to 40 mol %, the above radical (III), in which x=2 and n=1 and which derives from ethylenediamine, or the radical deriving from piperazine:

c) in the proportions of 0 to 20 mol %, the —NH—(CH$_2$)$_6$—NH— radical deriving from hexamethylenediamine, these polyaminoamides being crosslinked by addition of a bifunctional crosslinking agent chosen from epihalohydrins, diepoxides, dianhydrides or bisunsaturated derivatives, by means of 0.025 to 0.35 mol of crosslinking agent per amine group of the polyaminoamide, and alkylated by reaction with acrylic acid, with chloroacetic acid or with an alkanesultone, or with their salts.

The saturated carboxylic acids are preferably chosen from acids having 6 to 10 carbon acids, such as adipic, 2,2,4-trimethyl- and 2,4,4-trimethyladipic or terephthalic acid, acids containing an ethylenic double bond, such as, for example, acrylic, methacrylic and itaconic acids.

The alkanesultones used in the alkylation are preferably propane- or butanesultone and the salts of the alkylating agents are preferably the sodium or potassium salts.

(5) Polymers containing zwitterionic units of formula (IV):

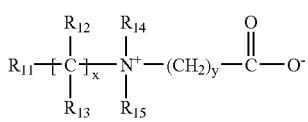

in which $R_{11}$ denotes a polymerizable unsaturated group, such as an acrylate, methacrylate, acrylamide or methacrylamide group, x and y represent an integer from 1 to 3, $R_{12}$ and $R_{13}$ represent hydrogen, methyl, ethyl or propyl and $R_{14}$ and $R_{15}$ represent a hydrogen atom or an alkyl radical, so that the sum of the carbon atoms in $R_{14}$ and $R_{15}$ does not exceed 10.

The polymers comprising such units can also contain units derived from non-zwitterionic monomers, such as vinylpyrrolidone, dimethyl- or diethylaminoethyl acrylate or methacrylate or alkyl acrylates or methacrylates, acrylamides or methacrylamides or vinyl acetate. Mention may be made, by way of example, of the methyl methacrylate/methyl dimethylcarboxymethyl! ammonioethylmethacrylate copolymer, such as the product sold under the name Diaformer by the company Sandoz.

(6) Polymers derived from chitosan containing monomer units corresponding to the following formulae:

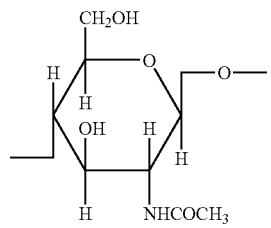

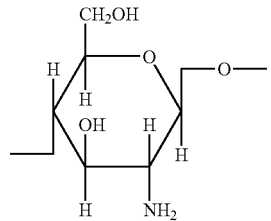

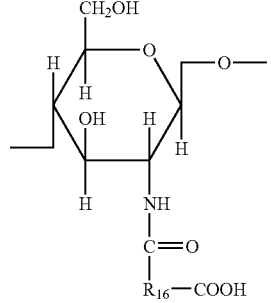

the D unit being present in proportions of from 0 to 30%, the E unit in proportions of from 5 to 50% and the F unit in proportions of from 30 to 90%, it being understood that, in this F unit, $R_{16}$ represents a radical of formula:

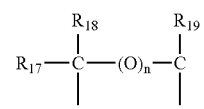

in which, if n=0, $R_{17}$, $R_{18}$ and $R_{19}$, which are identical or different, each represent a hydrogen atom, a methyl, hydroxyl, acetoxy or amino residue, a monoalkylamino residue or a dialkylamino residue, which are optionally interrupted by one or a number of nitrogen atoms and/or optionally substituted by one or a number of amino, hydroxyl, carboxyl, alkylthio or sulpho groups, or an alkylthio residue, in which the alkyl group carries an amino residue, at least one of the $R_{17}$, $R_{18}$ and $R_{19}$ radicals being, in this case, a hydrogen atom;

or, if n=1, $R_{17}$, $R_{18}$ and $R_{19}$ each represent a hydrogen atom, and the salts formed by these compounds with bases or acids.

(7) Polymers derived from the N-carboxyalkylation of chitosan, such as N-(carboxymethyl)chitosan or N-(carboxybutyl)chitosan sold under the name "Evalsan" by the company Jan Dekker.

(8) Polymers corresponding to the general formula (V) described in French Patent 1,400,366, the disclosure of which is hereby incorporated by reference:

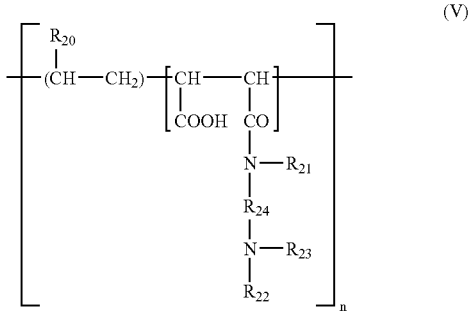

in which $R_{20}$ represents a hydrogen atom or a $CH_3O$, $CH_3CH_2O$ or phenyl radical $R_{21}$ denotes hydrogen or a lower alkyl radical, such as methyl or ethyl, $R_{22}$ denotes hydrogen or a lower alkyl radical, such as methyl or ethyl, and $R_{23}$ denotes a lower alkyl radical, such as methyl or ethyl, or a radical corresponding to the formula: $-R_{24}-N(R_{22})_2$, $R_{24}$ representing a $-CH_2-CH_2-$, $-CH_2-CH_2-CH_2-$ or $-CH_2-CH(CH_3)$-group and $R_{22}$ having the meanings mentioned above, and the higher homologues of these radicals containing up to 6 carbon atoms.

(9) Amphoteric polymers of the -A-Z-A-Z type chosen from:

a) the polymers obtained by reacting chloroacetic acid or sodium chloroacetate with compounds containing at least one unit of formula:

-A-Z-A-Z-A- (VI)

where A denotes a radical

and Z denotes the B or B' symbol, B or B', which are identical or different, denote a divalent radical which is a straight- or branched-chain alkylene radical containing up to 7 carbon atoms in the main chain, which is unsubstituted or substituted by hydroxyl groups, and which can additionally contain oxygen, nitrogen or sulphur atoms or 1 to 3 aromatic and/or heterocyclic rings; the oxygen, nitrogen and sulphur atoms being present in the form of ether, thioether, sulphoxide, sulphone, sulphonium, alkylamine or alkenylamine groups or hydroxyl, benzylamine, amine oxide, quaternary ammonium, amide, imide, alcohol, ester and/or urethane groups.

b) The polymers of formula:

-A-Z-A-Z- (VI')

where A denotes a radical

and Z denotes the B or B' symbol and at least once B', B having the meaning indicated above and B' is a divalent radical which is a straight- or branched-chain alkylene radical having up to 7 carbon atoms in the main chain, the radical being unsubstituted or substituted by one or a number of hydroxyl radicals, and containing one or a number of nitrogen atoms, the nitrogen atom being substituted by an alkyl chain optionally interrupted by an oxygen atom and necessarily containing one or a number of carboxyl functional groups or one or a number of hydroxyl functional groups betainized by reaction with chloroacetic acid or sodium chloroacetate.

(10) $(C_1-C_5)$alkyl vinyl ether/maleic anhydride copolymers in which the maleic anhydride has been partially modified by semiamidification with an N,N-dialkylaminoalkylamine, such as N,N-dimethylaminopropylamine, or by semiesterification with an N,N-dialkanolamine. These copolymers can also contain other vinyl comonomers, such as vinylcaprolactam.

The particularly preferred amphoteric polymers according to the invention are those from the family (3), such as the copolymers whose CTFA name is Octylacrylamide/acrylates/butylaminoethyl methacrylate copolymer, such as the products sold under the name Amphomer or Lovocryl 47 by the company National Starch.

The fixing and/or conditioning polymer or polymers are, for example, present in concentrations of from 0.1% to 20% by weight, and preferably in concentrations of from 1% to 10% by weight, with respect to the total weight of the composition.

The concentration of acrylic copolymer is generally from 0.01 to 15% by weight with respect to the total weight of the composition and preferably from 0.05 to 8% by weight.

The ratio by weight of the fixing and/or conditioning polymer to the acrylic copolymer can be from 0.1:1 to 10:1 and preferably from 0.5:1 to 5:1.

The cosmetically acceptable medium is preferably composed of water or a mixture of water and of cosmetically acceptable solvents, such as monoalcohols, polyalcohols or glycol ethers, which can be used alone or as a mixture.

Mention may more particularly be made of lower alcohols, such as ethanol or isopropanol, polyalcohols, such as diethylene glycol, or glycol ethers, such as the alkyl ethers of glycol or of diethylene glycol.

The concentration of solvents is generally from 0 to 80% by weight and preferably from 0 to 55% by weight with respect to the total weight of the composition.

The cosmetically acceptable medium is preferably composed essentially of water.

The pH of the compositions according to the invention is generally from 2 to 9 and in particular from 3 to 8. It can be adjusted to the chosen value by means of basifying or acidifying agents commonly used in cosmetics for this type of application.

When the composition according to the invention is pressurized in the form of an aerosol, for the purpose of obtaining a lacquer, it comprises at least one propellant agent which can be chosen from volatile hydrocarbons, such as n-butane, propane, isobutane or pentane, chlorinated and/or fluorinated hydrocarbons and their mixtures. Carbon dioxide gas, nitrous oxide, dimethyl ether, nitrogen, compressed air and their mixtures can also be used as propellant agent.

The concentration of propellant is generally from 10 to 50% by weight with respect to the total weight of the pressurized composition and preferably from 15 to 35% by weight.

The compositions according to the invention, whether pressurized or not, can additionally contain surface-active agents, preserving agents, sequestrants, softeners, fragrances, dyes, viscosity-modifying agents, foam-modifying agents, antifoaming agents, pearlescence agents, moisturizing agents, anti-dandruff agents, anti-seborrhoeic agents, sunscreening agents, proteins, vitamins, plasticizers, hydroxy acids and electrolytes.

The compositions according to the invention can also contain other conditioning agents. The latter may then be chosen from natural or synthetic oils and waxes, fatty alcohols, esters of polyhydric alcohols, glycerides, silicone gums and resins or mixtures of these various compounds.

Of course, the person skilled in the art will be careful to choose the optional compound or compounds to be added to the composition according to the invention so that the advantageous properties intrinsically attached to the composition in accordance with the invention are not, or not substantially, detrimentally affected by the addition envisaged.

The compositions used according to the invention are, for example, rinsed or non-rinsed hair compositions.

They are more particularly hair-setting lotions, lotions for blow-drying, fixing compositions (lacquers) and styling compositions. The lotions can be packaged in various forms, in particular in atomizers or pump-action sprays or in aerosol containers, in order to ensure application of the composition in the vaporized form.

A further subject of the invention is a process for the cosmetic treatment of keratinous substances, such as hair, characterized in that it consists in applying a cosmetic composition as defined above to keratinous substances and in then optionally rinsing with water, after an optional setting time.

Concrete but in no way limiting examples will now illustrate the invention.

In the examples, AM means active material.

EXAMPLE 1

Two compositions A and B according to the invention were prepared and were compared with compositions C and D each containing a single one of the two polymers. The four compositions were packaged in a pump-action spray. A panel of 5 experienced testers evaluated the appearance of the spray and the presence or the absence of foam at the outlet of the container or on the hair.

In order to evaluate the appearance of the spray, the grading ranged from 0 (bad), meaning that the spray was not diffuse and that the sprayed droplets were not fine, to 5 (excellent), which meant that the spray was highly diffuse and that the sprayed droplets were very fine.

In order to evaluate the presence or the absence of foam at the outlet of the container or on the hair, the grading ranged from 0 (bad), meaning that there was an unacceptable copious foam, to 5 (excellent), which meant that there was no foam at all.

The results are collated/in the table below:

| In g AM | A | B | C | D |
|---|---|---|---|---|
| Ultrahold Strong[1] | 6 | 4 | 8 | — |
| Amerhold DR 25[2] | 2 (as copolymer) | 4 (as copolymer) | — | 8 (as copolymer) |
| AMP[3], q.s. | pH 9 | pH 9 | pH 9 | pH 9 |
| Water, q.s. for | 100 | 100 | 100 | 100 |
| Appearance of the spray | 4 | 5 | 1 | 3 |

-continued

| In g AM | A | B | C | D |
|---|---|---|---|---|
| Absence or presence of foam | 4 | 5 | 1 | 4.5 |

[1]Ultrahold Strong from BASF: acrylic acid/ethyl acrylate/N-tert-butylacrylamide terpolymer.
[2]Amerhold DR 25 from Amerchol: ethyl acrylate/methyl methacrylate/methacrylic acid/acrylic acid copolymer having a glass transition temperature of approximately 30° C. as an aqueous dispersion comprising 25% by weight of the acrylic copolymer.
[3]AMP: 2-Amino-2-methylpropanol.

The compositions A and B according to the invention had better results as can be seen in the table.

EXAMPLE 2

Two compositions E and F according to the invention were prepared and were compared with compositions G and H each containing a single one of the two polymers. The four compositions were packaged in a pump-action spray. A panel of 5 experienced testers evaluated the appearance of the spray and the presence or the absence of foam at the outlet of the container or on the hair.

In order to evaluate the appearance of the spray, the grading ranged from 0 (bad), meaning that the spray was not diffuse and that the sprayed droplets were not fine, to 5 (excellent), which meant that the spray was highly diffuse and that the sprayed droplets were very fine.

In order to evaluate the presence or the absence of foam at the outlet of the container or on the hair, the grading ranged from 0 (bad), meaning that there was an unacceptable copious foam, to 5 (excellent), which meant that there was no foam at all.

The results are collated in the table below:

| In g AM | E | F | G | H |
|---|---|---|---|---|
| Lovocryl 47[1] | 6 | 4 | 8 | — |
| Amerhold DR 25[2] | 2 (as copolymer) | 4 (as copolymer) | — | 8 (as copolymer) |
| AMP[3], q.s. pH | 9 | 9 | 9 | 9 |
| Water, q.s. for | 100 | 100 | 100 | 100 |
| Appearance of the spray | 5 | 5 | 2 | 3 |
| Absence or presence of foam | 5 | 5 | 3 | 4.5 |

[1]Lovocryl 47 from National Starch: Octylacrylamide/acrylates/butylaminoethyl methacrylate copolymer (CTFA).
[2]Amerhold DR 25 from Amerchol: ethyl acrylate/methyl methacrylate/methacrylic acid/acrylic acid copolymer having a glass transition temperature of approximately 30° C. as an aqueous dispersion comprising 25% by weight of the acrylic copolymer.
[3]AMP: 2-Amino-2-methylpropanol.

The compositions E and F according to the invention had a diffuse spray and there was no foam at the outlet of the pump-action spray or on the hair.

EXAMPLE 3

A composition J according to the invention was prepared and was compared with the compositions K and L, each containing a single one of the two polymers. The three compositions were packaged as an aerosol. A panel of 5 experienced testers evaluated the appearance of the spray and the absence or the presence of foam at the outlet of the container or on the hair.

In order to evaluate the appearance of the spray, the grading ranged from 0 (bad), meaning that the spray was not diffuse and that the sprayed droplets were not fine, to 5 (excellent), which meant that the spray was highly diffuse and that the sprayed droplets were very fine.

In order to evaluate the presence or the absence of foam at the outlet of the container or on the hair, the grading ranged from 0 (bad), meaning that there was an unacceptable copious foam, to 5 (excellent), which meant that there was no foam at all.

The results are collated in the table below:

| In g AM | J | K | L |
|---|---|---|---|
| Ultrahold Strong[(1)] | 2 | 4 | — |
| Amerhold DR 25[(2)] | 2 | — | 4 |
|  | (as copolymer) |  | (as copolymer) |
| AMP[(3)], q.s. pH | 7 | 7 | 7 |
| Ethanol | 20 | 20 | 20 |
| Water | 41 | 41 | 41 |
| DME[(4)] | 35 | 35 | 35 |
| Appearance of the spray | 5 | 2 | 4 |
| Absence of foam | 5 | 1 | 4 |

[(1)]Ultrahold Strong from BASF: acrylic acid/ethyl acrylate/N-tert-butylacrylamide terpolymer.
[(2)]Amerhold DR 25 from Amerchol: ethyl acrylate/methyl methacrylate/methacrylic acid/acrylic acid copolymer having a glass transition temperature of approximately 30° C. as an aqueous dispersion comprising 25% by weight of the copolymer.
[(3)]AMP: 2-Amino-2-methylpropanol.
[(4)]DME: Dimethyl ethyl (propellant).

The composition J according to the invention had a diffuse spray and there was no foam at the outlet of the aerosol or on the hair.

EXAMPLE 4

A concrete example is given here of a composition according to the invention pressurized as an aerosol with the following composition:

| | | |
|---|---|---|
| Octylacrylamide/acrylates/butylaminoethyl methacrylate copolymer (Lovocryl 47 from National Starch) | | 2 g AM |
| Ethyl acrylate/methyl methacrylate/methacrylic acid/acrylic acid terpolymer sold as an aqueous dispersion containing 25% of AM under the name Amerhold DR 25 by Amerchol | | 3 g AM |
| 2-Amino-2-methyl-1-propanol | q.s. | pH 9 |
| Ethanol | | 20 g |
| Dimethyl ether | | 35 g |
| Water | q.s. for | 100 g |

EXAMPLE 5

A concrete example is given here of a composition according to the invention packaged in a pump-action spray with the following composition:

| | | |
|---|---|---|
| Dimethylaminoethyl methacrylate/vinylcaprolactam/vinylpyrrolidone terpolymer | | 2 g AM |
| as a solution in ethanol containing 37% of AM (Gaffix VC 713 from ISP) | | |
| Ethyl acrylate/methyl methacrylate/methacrylic acid/acrylic acid terpolymer sold as an aqueous dispersion containing 25% of AM under the name Amerhold DR 25 by Amerchol | | 2 g AM |
| 2-Amino-2-methyl-1-propanol | q.s. | pH 7 |
| Water | q.s. for | 100 g |

EXAMPLE 6

A concrete example is given here of a composition according to the invention packaged in a pump-action spray with the following composition:

| | | |
|---|---|---|
| Methacrylic acid/hydroxyester methacrylate/butyl acrylate/methyl methacrylate tetrapolymer sold as an aqueous dispersion containing 41% of active material under the name Acudyne 255 by the company Seppic | | 4 g AM |
| Ethyl acrylate/methyl methacrylate/methacrylic acid/acrylic acid terpolymer sold as an aqueous dispersion containing 25% of AM under the name Amerhold DR 25 by Amerchol | | 2 g AM |
| 2-Amino-2-methyl-1-propanol | q.s. | pH 7 |
| Water | q.s. for | 100 g |

What is claimed is:

1. A cosmetic composition comprising:
   an ethyl acrylate/methyl methacrylate/methacrylic acid/acrylic acid copolymer; and
   a polymer chosen from acrylates/hydroxyesters acrylates copolymers, wherein the ratio by weight of the at least one acrylates/hydroxyesters acrylates copolymers to the at least one ethyl acrylate/methyl methacrylate/methacrylic acid/acrylic acid copolymer is from 0.1:1 to 10:1.

2. A cosmetic composition according to claim 1, wherein said ethyl acrylate/methyl methacrylate/methacrylic acid/acrylic acid copolymer has a glass transition temperature of approximately 30° C. as an aqueous dispersion comprising 25% by weight of the copolymer.

3. A cosmetic composition comprising:
   an acrylates copolymer; and
   a polymer chosen from acrylates/hydroxyesters acrylates copolymers, wherein the ratio by weight of the acrylates/hydroxyesters acrylates copolymers to the acrylates copolymer is from 0.1:1 to 10:1.

4. A hair spray comprising:
   an ethyl acrylate/methyl methacrylate/methacrylic acid/acrylic acid copolymer; and
   a polymer chosen from acrylates/hydroxyesters acrylates copolymers, wherein the ratio by weight of the acrylates/hydroxyesters acrylates copolymers to the ethyl acrylate/methyl methacrylate/methacrylic acid/acrylic acid copolymer is from 0.1:1 to 10:1.

5. A hair spray according to claim 4, wherein said ethyl acrylate/methyl methacrylate/methacrylic acid/acrylic acid copolymer has a glass transition temperature of approximately 30° C. as an aqueous dispersion comprising 25% by weight of the copolymer.

6. A hair spray according to claim 5, further comprising a propellant.

7. A hair spray according to claim 6, wherein said propellant is chosen from fluorinated hydrocarbons.

8. A hair spray comprising:
an acrylates copolymer; and
a polymer chosen from acrylates/hydroxyesters acrylates copolymers, wherein the ratio by weight of the acrylates/hydroxyesters acrylates copolymers to the acrylates copolymer is from 0.1:1 to 10:1.

9. A hair spray according to claim 8, further comprising a propellant.

10. A cosmetic composition comprising:
an ethyl acrylate/methyl methacrylate/methacrylic acid/acrylic acid copolymer;
a polymer chosen from acrylates/hydroxyesters acrylates copolymers;
water; and
an alcohol;
wherein the ratio by weight of the acrylates/hydroxyesters acrylates copolymers to the ethyl acrylate/methyl methacrylate/methacrylic acid/acrylic acid copolymer is from 0.1:1 to 10:1.

11. A cosmetic composition according to claim 10, further comprising:
aminomethylpropanol;
a fragrance;
a preserving agent;
a conditioning agent;
a basifying agent other than aminomethylpropanol; and
a protein.

12. A hair spray comprising:
an ethyl acrylate/methyl methacrylate/methacrylic acid/acrylic acid copolymer;
a polymer chosen from acrylates/hydroxyesters acrylates copolymers;
water; and
an alcohol;
wherein the ratio by weight of the acrylates/hydroxyesters acrylates copolymers to the ethyl acrylate/methyl methacrylate/methacrylic acid/acrylic acid copolymer is from 0.1:1 to 10:1.

13. A hair spray according to claim 12 further comprising:
aminomethylpropanol;
a fragrance;
a preserving agent;
a conditioning agent;
a basifying agent other than aminomethylpropanol; and
a protein.

14. A hair spray according to claim 12 wherein said ethyl acrylate/methyl methacrylate/methacrylic acid/acrylic acid copolymer is at least partially neutralized.

15. A cosmetic composition comprising:
an acrylates copolymer; and
a methacrylic acid/hydroxyester methacrylate/butyl acrylate/methyl methacrylate tetrapolymer, wherein the ratio by weight of the methacrylic acid/hydroxyester methacrylate/butyl acrylate/methyl methacrylate tetrapolymer to the acrylates copolymer is from 0.1:1 to 10:1.

16. A cosmetic composition according to claim 15 wherein said methacrylic acid/hydroxyester methacrylate/butyl acrylate/methyl methacrylate tetrapolymer is an aqueous dispersion containing 41% of active material.

17. A hair spray comprising:
an ethyl acrylate/methyl methacrylate/methacrylic acid/acrylic acid copolymer; and
a methacrylic acid/hydroxyester methacrylate/butyl acrylate/methyl methacrylate tetrapolymer, wherein the ratio by weight of the methacrylic acid/hydroxyester methacrylate/butyl acrylate/methyl methacrylate tetrapolymer to the ethyl acrylate/methyl methacrylate/methacrylic acid/acrylic acid copolymer is from 0.1:1 to 10:1.

18. A hair spray according to claim 17, wherein said methacrylic acid/hydroxyester methacrylate/butyl acrylate/methyl methacrylate tetrapolymer is an aqueous dispersion containing 41% of active material.

19. An aerosol hair spray comprising:
an ethyl acrylate/methyl methacrylate/methacrylic acid/acrylic acid copolymer; and
a methacrylic acid/hydroxyester methacrylate/butyl acrylate/methyl methacrylate tetrapolymer, wherein the ratio by weight of the methacrylic acid/hydroxyester methacrylate/butyl acrylate/methyl methacrylate tetrapolymer to the ethyl acrylate/methyl methacrylate/methacrylic acid/acrylic acid copolymer is from 0.1:1 to 10:1.

20. A pump action hair spray comprising:
an ethyl acrylate/methyl methacrylate/methacrylic acid/acrylic acid copolymer; and
a methacrylic acid/hydroxyester methacrylate/butyl acrylate/methyl methacrylate tetrapolymer, wherein the ratio by weight of the methacrylic acid/hydroxyester methacrylate/butyl acrylate/methyl methacrylate tetrapolymer to the ethyl acrylate/methyl methacrylate/methacrylic acid/acrylic acid copolymer is from 0.1:1 to 10:1.

21. A pump action hair spray comprising:
an ethyl acrylate/methyl methacrylate/methacrylic acid/acrylic acid copolymers
a polymer chosen from acrylates/hydroxyesters acrylates copolymers;
water; and
an alcohol;
wherein the ratio by weight of the acrylates/hydroxyesters acrylates copolymers to the ethyl acrylate/methyl methacrylate/methacrylic acid/acrylic acid copolymer is from 0.1:1 to 10:1.

22. A hair spray according to claim 21 further comprising:
aminomethylpropanol;
a fragrance;
a preserving agent;
a conditioning agent;
a basifying agent other than aminomethylpropanol; and
a protein.

23. An aerosol hair spray comprising:
an ethyl acrylate/methyl methacrylate/methacrylic acid/acrylic acid copolymers
a polymer chosen from acrylates/hydroxyesters acrylates copolymers;
water;
propellant; and
an alcohol;
wherein the ratio by weight of the acrylates/hydroxyesters acrylates copolymers to the ethyl acrylate/methyl methacrylate/methacrylic acid/acrylic acid copolymer is from 0.1:1 to 10:1.

24. A hair spray according to claim 23 further comprising:
aminomethylpropanol;
a fragrance;
a preserving agent;
a basifying agent other than aminomethylpropanol; and
a protein.

* * * * *

UNITED STATES PATENT AND TRADEMARK OFFICE
CERTIFICATE OF CORRECTION

| | | |
|---|---|---|
| PATENT NO. | : 7,029,661 B1 | Page 1 of 1 |
| APPLICATION NO. | : 09/172853 | |
| DATED | : April 18, 2006 | |
| INVENTOR(S) | : Christine Dupuis | |

It is certified that error appears in the above-identified patent and that said Letters Patent is hereby corrected as shown below:

In claim 21, column 18, line 32, "copolymers" should read --copolymer;--.

In claim 23, column 18, line 50, "copolymers" should read --copolymer;--.

In claim 24, column 18, line 63, following "a preserving agent;" insert --a conditioning agent;--.

Signed and Sealed this

Twenty-fifth Day of July, 2006

JON W. DUDAS
*Director of the United States Patent and Trademark Office*